United States Patent [19]

Turner, Sr.

[11] Plant 5,233

[45] May 15, 1984

[54] TRICOLOR VARIEGATED PITTOSPORUM PLANT

[76] Inventor: Ted L. Turner, Sr., 6503 S. Padre Island Dr., Corpus Christi, Tex. 78412

[21] Appl. No.: 445,727

[22] Filed: Nov. 29, 1982

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Stewart N. Rice

[57] ABSTRACT

A pittosporum plant which has a dwarf habit of growth and having leaf blades which are variegated, there being irregularly shaped areas of three different colors present on the variegated leaves, such being dark green, medium green and pale yellow. The variegated leaves do not have a uniform pattern of variegation, and the pattern of variegation differs from leaf to leaf.

1 Drawing Figure

DESCRIPTION OF THE INVENTION

The present invention relates to a new and distinct variety of pittosporum plant of the variety *Pittosporum tobira,* which originated and was discovered by me as a cultivated sport of the variety known as "Wheeler's dwarf". The sport was discovered by me on a *Pittosporum tobira* "Wheeler's dwarf" being grown and cultivated by me in a nursery in Corpus Christi, Tex. Upon discovery of the sport, I observed that substantially all of the leaves of the sport, unlike the dark green leaves of the parent plant, were variegated with three colors present, such being dark green, medium green and pale yellow. In order to determine whether or not the sport would asexually reproduce, I performed an initial experiment wherein I made two cuttings from the sport, and from such two cuttings I was able to asexually reproduce about 20 plants on their own roots, all of which plants had the same characteristics as the sport, and all four of which constituted a new and distinct variety of pittosporum. In the initial experiment, only about four of the cuttings did not survive.

Subsequent to the initial experiment, in due course I asexually reproduced numerous of the new and distinct variety of pittosporum from other cuttings of the original sport, as well as from cuttings from the first generation plants grown in the initial experiment described above, and all of the descendant plants show the same characteristics as the original sport. As a result of extensive observations and tests which are not described in full herein for sake of brevity, it is my opinion and I am convinced that my new plant is a new variety of pittosporum which is distinguished from all other varieties of which I am aware as evidenced by the following unique combination of principal characteristics which are outstanding therein:

(1) A dwarf and compact habit of growth makes it especially suitable as a border plant, as a small hedge, in planter boxes and as a pot plant;

(2) A slow rate of growth which is advantageous in that frequent pruning is not necessary to maintain the shrub in a pleasing shape;

(3) An ability to be asexually reproduced;

(4) The ability to provide a shrub having three colors by reason of the variegated nature of broadleaf evergreen leaves occuring on the new variety, the variegation consisting of irregular shaped areas of dark green, medium green and pale yellow, with the dark green area of a leaf generally being in the central base area of the leaf, and the medium green and pale yellow areas generally forming an irregular margin area on each leaf, the pattern of variegation varying from leaf to leaf, and which leaves grow alternately in a whorl on the branches;

(5) The ability to tolerate pruning in order that attractive shapes can be maintained.

Asexual reproductions of my new variety as by cuttings shows that the foregoing charateristics and distinction come true to form and are established and transmitted through succeeding propagations.

Although all or substantially all of the leaves on the plant of my new variety are variegated with three colors as herein described, there may be and usually are present some leaves which are not variegated but are dark green like the leaves of the parent plant. These non-variegated leaves may be entirely eliminated from successive generations of plants but have not been completely eliminated from all of the plants grown to date.

The accompanying FIG. 1 shows a typical young specimen plant of my new variety and the variegated nature and color of leaves thereof. Even though the plant illustrated in FIG. 1 is young, the leaves are mature leaves and the colors shown are the colors for the mature leaves and are not the colors for new leaves hereafter described. The true color of the foliage is described in the following description and is best depicted by the views in the figures which depict the color as nearly as true as is reasonably possible in a color illustration of this type.

The following is a detailed description of my new variety of pittosporum, with color numbers in accordance with the Pantone Matching System of colors for printing inks, 16th edition, published by Pantone, Inc., 1977. Terms used to describe colors are those of ordinary significance.

THE PLANT

Parentage: A cultivated sport of "Wheeler's dwarf" variety of *Pittosporum tobira.*

Growth habit: Compact, dwarf; slow growing; the height of an unpruned mature plant will probably be from about 1.5 to 2 meters, but has not yet been determined. The plant grows full from just above ground level upward, with the width of the plant about the same as the height.

Hardiness: Adapted to seaside planting; tolerates droughts; will not withstand prolonged and severe freezing weather; most suitable for the Southern United States from California to Florida, in the areas known as Zones 9 and 10.

Branches: The plant is tightly branched from just above ground level with main branches ascending and with branching at each node. The plant does not develop a central leader or trunk. New growth of branches is light green changing to light brown and later to dark brown as branches mature.

Foliage:

*Type.*—Broadleaf evergreen; petioled; grow alternately in a whorl on branches.

*Shape.*—Oblanceolate, more or less, with entire margins. Apex is obtuse, and base is acuminate.

*Petioles.*—Length — from about 3 to 5 mm; color light green.

*Leaf size.*—Length of mature leaf from about 4 to 8 cm; width of mature leaf about 13 to 25 mm. Size of leaf varies according to sunshine conditions at the time the leaf is produced, with larger leaves being produced under cloudy conditions than under sunny conditions.

*Venation.*—Pinnately. Midrib on under surface prominent and readily apparent; on upper surface midrib is clearly visible and pronounced, and is of a lighter color than surrounding areas of the leaf; lateral veins are not readily apparent.

*Color of variegated leaves.*—Mature leaves: upper surface — dark green, Color No. 350C, with variegated margins comprised of irregularly shaped areas of medium green, Color No. 392U, and of pale yellow, Color No. 113U; the line of intersection between the green of the central area and the margin being relatively sharp, but being an irregular line such that the depth of the margin is very irregular and sometimes occupies the entire tip, or outer half, of a leaf blade, the width of the margin generally varying from about 1 to 10 mm; the pattern of variegation is not uniform and varies from leaf to leaf; under surface — similar to the upper surface but lighter colors. New leaves: upper surface — generally darker than mature leaves with the three colors being dark green, Color No. 378U and light green, Color No. 390U; nature and width of margins same as on mature leaves. Most of the variegation is on the outer half (tip) of the leaf blade. The dark green, Color No. 350C, of a mature leaf is the same as the dark green of tne non-variegated "Wheeler's dwarf" variety of the parent plant.

*Leaf texture.*—Tough, leathery; smooth; upper surface — semi-glossy; lower surface — dull.

*Flowers.*—The nature of the flowers that will be produced has not been determined. Flowers of the parent and of related plants are an ivory color, each flower being about 15 mm in diameter; and, it is expected that the flowers on the plant herein claimed and described will be similar to those on the parent.

To further describe my new variety of pittosporum, it is very similar in size and growth habit to the "Wheeler's dwarf" variety of *Pittosporum tobira* except for the variegated nature of substantially all of the leaf blades on my new variety, and except that my new variety is slower growing than the "Wheeler's dwarf". The dark green portion (Color No. 350C) of the mature leaves on my new variety is substantially the same green as the green of the "Wheeler's dwarf".

There is a variegated form of *Pittosporum tobira* known as *Pittosporum tobira variegata.* My new variety differs from *Pittosporum tobira variegata* in that it is slower growing and in that my new variety has a dwarf habit of growth. Also the leaves on the *Pittosporum tobira variegata* have only two colors in the variegation, the leaf blades of the *Pittosporum tobira variegata* having a creamy white margin.

I have also discovered a new and distinct variety of pittosporum plant of the variety *Pittosporum tobira* the leaf blades of which have a variegated pattern consisting of only two colors, that is of (1) said medium green color no. 392U, and of (2) said pale yellow Color No. 113U in the margins. The said new variety having only two colors is the subject of my U.S. Plant Pat. No. 4,919 issued Nov. 2, 1982.

VARIETY NAME

The proposed variety name of my new plant is *Pittosporum tobira* "Turner's Dwarf Tricolor".

I claim:

1. A new and distinct variety of pittosporum, substantially as herein shown and described, characterized particularly as to novelty by the unique combination of: A dwarf and compact habit of growth makes it especially suitable as a border plant, as a small hedge, in planter boxes and as a pot plant; a slow rate of growth which is advantageous in that frequent pruning is not necessary to maintain the shrub in a pleasing shape; an ability to be asexually reproduced; the ability to provide a shrub having three colors by reason of the variegated nature of all or substantially all of the broadleaf evergreen leaves occuring on the new variety, the variegation consisting of irregular shaped areas of dark green, medium green and pale yellow, with the dark green area of a leaf generally being in the central base area of the leaf, and the medium green and pale yellow areas generally forming an irregular margin area on each leaf, the pattern of variegation varying from leaf to leaf, and which leaves grow alternately in a whorl on the branches; and the ability to tolerate pruning in order that attractive shapes can be maintained.

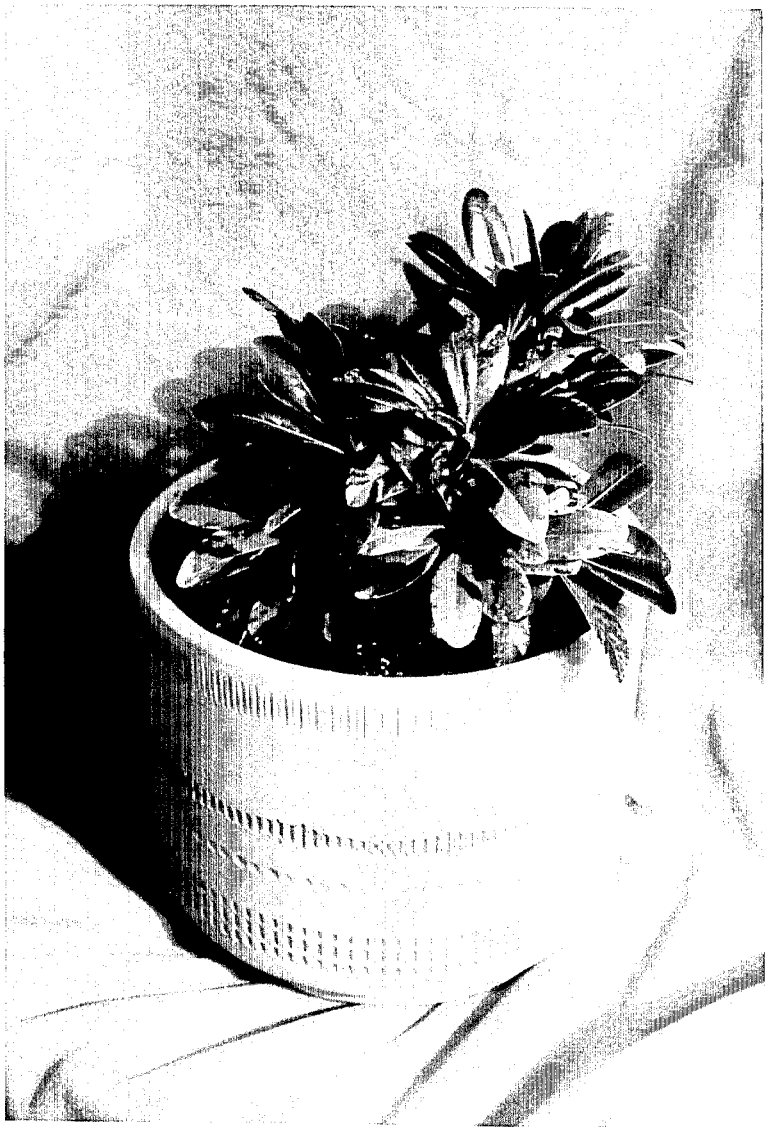

* * * * *